United States Patent [19]
Sato et al.

[11] Patent Number: 4,862,066
[45] Date of Patent: Aug. 29, 1989

[54] OIL LEAKAGE SENSOR ELEMENT

[75] Inventors: Yoshiaki Sato; Tazuru Ishikawa, both of Saitama, Japan

[73] Assignee: Junkosha Co., Ltd., Japan

[21] Appl. No.: 235,461

[22] Filed: Aug. 24, 1988

[30] Foreign Application Priority Data

Aug. 31, 1987 [JP] Japan ................. 62-217103

[51] Int. Cl.$^4$ ............................................... H01L 7/00
[52] U.S. Cl. .................................... 324/65 P; 338/34; 204/430
[58] Field of Search ................. 340/620; 73/337, 338; 338/34, 225; 324/65 R, 65 P; 204/430

[56] References Cited

U.S. PATENT DOCUMENTS

| | | | |
|---|---|---|---|
| 4,082,997 | 4/1978 | Ohtsu | 338/225 |
| 4,125,822 | 11/1978 | Perren | 338/34 |
| 4,142,400 | 3/1979 | Colla | 338/34 |
| 4,631,952 | 12/1986 | Donaghey | 338/34 |

*Primary Examiner*—Reinhard J. Eisenzopf
*Assistant Examiner*—Jose M. Solis
*Attorney, Agent, or Firm*—Mortenson & Uebler

[57] ABSTRACT

An oil leakage sensor element is provided wherein a plurality of electrical conductors are contained within and separated from each other by a continuously porous polytetrafluoroethylene (PTFE) material containing from 15 to 40 weight percent carbon particles, the carbon particles having irregular shapes and average diameter between 10 and 30 millimicrons, at least a portion of the exterior surfaces of the carbon particles being exposed at the pore walls of the PTFE and extending into the pores. The porous PTFE material is preferably obtained by stretching an extruded, unsintered PTFE film containing the carbon particles, after removal of lubricant, to a draw ratio of 1.5 times or less. The sensor element, in use, is connected between electrodes which, in turn, are connected to an alarm device. Preferably, the sensor is connected to elongate conductors (wires) such that the direction of stretch of the material is aligned with the lengthwise direction of the conductors.

6 Claims, 2 Drawing Sheets

OIL LEAKAGE SENSOR ELEMENT

BACKGROUND OF THE INVENTION

The present invention relates to an oil leakage sensor element which detects leakage of oil onto a water surface by means of a change in electrical resistance.

A conventional oil leakage sensor element is an element in which two conductors are separated by a polytetrafluoroethylene (PTFE) film containing carbon particles. When oil leaks onto the surface of water in which this sensor element is installed, the oil permeates the areas between the carbon particles inside the resin, and lowers conductivity arising from the tunnel effect. This causes a change in the electrical resistance value of the sensor element, and the oil leakage is detected as a result of this change in electrical resistance.

In the case of the abovementioned conventional sensor element, the PTFE is unsatisfactory in terms of permeability to high-viscosity oils such as heavy oils, especially grade C heavy oils, and vegetable oils. Furthermore, most of the carbon particles are surrounded by PTFE. As a result, the leaking oil does not achieve sufficient contact with the carbon particles. Consequently, the change in the electrical resistance value of the sensor element at the time of oil leakage is small, so that the oil leakage detection sensitivity is unsatisfactory.

The present invention was designed in light of the abovementioned problems encountered in the prior art. The object of the present invention is to increase the change in the electrical resistance value of an oil leakage sensor element by improving the permeability of the element to high-viscosity heavy oils, and sufficiently increasing the contact of the oils with the carbon particles in the element.

SUMMARY OF THE INVENTION

An oil leakage sensor element is provided comprising a plurality of electrical conductors contained within and separated from each other by a continuously porous, stretched polytetrafluoroethylene (PTFE) material containing from 15 to 40 weight percent carbon particles, the carbon particles having irregular shapes and average diameter between 10 and 30 millimicrons, at least a portion of the exterior surface of the carbon particles being exposed at the pore walls of the PTFE and extending into the pores. The porous, extruded PTFE film containing the carbon particles is stretched, after removal of lubricant, to an extent of 1.5 times or less its unstretched length. The sensor element in use is connected between electrodes, which electrodes are connected to resistance metering apparatus. The electrodes may be wires and the element is preferably connected to the wires such that the direction of stretch of the material is aligned with the lengthwise direction of the wires.

DETAILED DESCRIPTION OF THE INVENTION AND PREFERRED EMBODIMENTS WITH REFERENCE TO THE DRAWINGS

An oil leakage sensor element is provided wherein a plurality of electrical conductors are contained within and separated from each other by a continuously porous polytetrafluoroethylene (PTFE) material containing from 15 to 40 weight percent carbon particles, the carbon particles having irregular shapes and average diameter between 10 and 30 millimicrons, at least a portion of the exterior surfaces of the carbon particles being exposed at the pore walls of the PTFE and extending into the pores. The porous PTFE material is preferably obtained by stretching an extruded, unsintered PTFE film containing the carbon particles, after removal of lubricant, to a draw ratio of 1.5 times or less. The sensor element, in use, is connected between electrodes which, in turn, are connected to an alarm device. Preferably, the sensor is connectede to elongate conductors (wires) such that the direction of stretch of the material is aligned with the lengthwise direction of the conductors.

The oil leakage sensor element of the present invention is characterized by the fact that multiple conductors are separated from each other by a material which is formed by impregnating 15 to 40 weight percent carbon particles, which are 10 to 30 millimicrons in diameter and which have irregular surfaces so that their surface area is increased, into a continuously porous polytetrafluoroethylene, and in which the exterior surfaces of the aforementioned carbon particles are exposed at the pore walls of the PTFE.

Polytetrafluoroethylene containing a relatively large quantity of carbon particles has an electrical conduction mechanism which depends on three-dimensional chains of containing carbon particles. In the present invention, since the exterior surfaces of the carbon particles are exposed at the pore walls of the continuously porous resin, oil components can easily adhere to the exterior surfaces of the carbon particles following permeation of the resin by a high-viscosity oil. The exterior surface of the carbon particles are irregular so that the effective surface area of the carbon particles is increased. As a result, oil is securely adsorbed on the carbon particles and the conductivity of the carbon particles themselves drops as a result of oil absorption by the resin.

Figure 1:
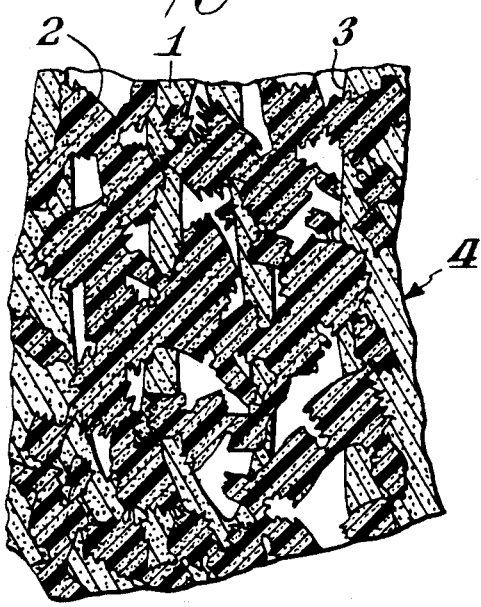
FIG. 1 is a conceptual diagram of the composite material used in the present invention under high magnification.
Figure 2:
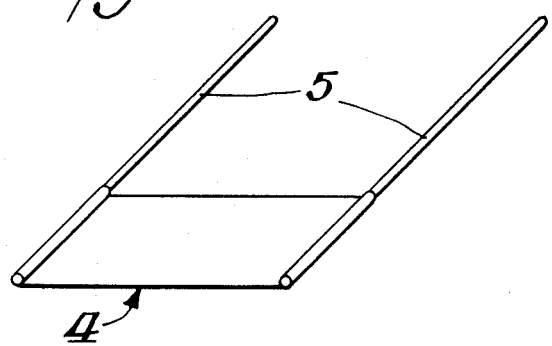
FIG. 2 is an oblique view of one embodiment of the oil leakage sensor element of the present invention connected between two wires.

FIGS. 1 and 2 illustrate a practical example of application of the present invention. In particular, FIG. 1 is a conceptual diagram under high magnification which illustrates the special features of the present invention.

In FIG. 1, polytetrafluoroethylene (PTFE) 1 constitutes a composite material 4 which contains carbon particles 2, and which has numerous pores 3 that connect with the outside of the material. Such pores 3 are formed by drawing PTFE 1 which contains carbon particles 2 by known techniques. As a result, the aforementioned composite material 4 is a stretched, porous PTFE 1 which contains carbon particles 2 and has pores 3 therein.

The aforementioned carbon particles 2 are small particles with diameters of 10 to 30 millimicrons. These particles have irregular structures, with numerous indentations and projections formed on the surfaces of the particles, so that the effective surface area of the particles is increased. The concentration of such carbon particles 2 in the PTFE 1 is 15 to 40 weight percent. Furthermore, relatively large pores 3 are formed by stretching this PTFE, so that numerous carbon particles 2 are exposed through the walls and inside the pores 3. A portion of the carbon particles are in contact with each other, so that the composite 4 is electrically conductive.

The aforementioned drawing of the PTFE 1 is performed at a draw ratio of 1.5 times or less. If the drawing exceeds this draw ratio, there is a danger that the drawing will damage the water resistance of the material 4. Accordingly, drawing at a draw ratio of approximately 1.2 to 1.4 times is desirable in order to maintain the aforementioned water resistance and at the same time form sufficient pores 3. In the case of drawing at a draw ratio of 1.3 times, the average diameter of the pores 3 in the resulting drawn PTFE will be approximately 0.5 micrometers (microns).

The oil leakage sensor element of the present invention is constructed by connecting a plurality of conductors 5 by means of the aforementioned material 4 as shown in FIG. 2. The material 4 used here has the form of a tape made up of the aforementioned film. The material 4 could also have a greater thickness, or could take the form of a cable. In FIG. 2, two conductors 5 are connected by the aforementioned material 4. It would also be possible to construct an oil leakage sensor element in which three or more conductors 5 are connected by the aforementioned material 4.

This oil leakage sensor element is installed so that the aforementioned material 4 is positioned at the surface of a quantity of water, and current is caused to flow between the aforementioned conductors 5. Leaking oil is detected by a change in the electrical resistance value of the sensor element. Specifically, the aforementioned material 4 is positioned at or near the aforementioned water surface. The pores 3 in the material are extremely small, and the material 4 itself is water-repellent. Accordingly, when no leaking oil is present, there is no invasion of the interiors of the pores 3 by water, and current flows between the conductors 5 in proportion to the quantity of carbon particles 2 contained in the material 4. At such time, the electrical resistance value between the conductors 5 is relatively low.

When oil leakage occurs, the oil spreads over the aforementioned surface of the water, and readily permeates the material 4 through the aforementioned pores 3. This oil adheres to the surfaces of the carbon particles 2 which are exposed at the walls of the pores 3. Because the surfaces of the carbon particles 2 have an increased area due to the aforementioned surface irregularities, the oil is securely adsorbed on the carbon particles 2. As a result, the carbon particles swell and increase in electrical resistance. Since the flow of current between the conductors 5 is achieved only through the carbon particles 2, the electrical resistance value between the conductors 5 is increased.

Because the surface area of the carbon particles 2 is increased by the formation of indentations and projections on the surfaces of the particles, the area of contact between the carbon particles 2 and the PTFE 1 is also increased. Accordingly, the carbon particles 2 which are exposed at the walls of the pores 3 are securely held by the PTFE 1 even in configurations where the particles are only partially embedded in the PTFE, or where projecting portions of the particles are stuck into the PTFE 1. As a result, the element of the present invention has improved durability, i.e., the carbon particles 2 will not fall out of the pores 3 even in long-term use.

Experiments which were performed in order to confirm the effect of making the aforementioned PTFE 1 porous will be described below.

Figure 3:
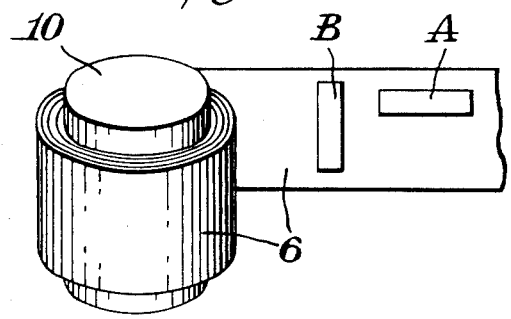
FIG. 3 is a schematic view of the material used in the invention in tape form wound about a core and which is referred to in the examples discussed below.

The carbon particles used were furnace-type carbon particles. Their commercial names are MA600, manufactured by Mitsubishi Kasei Kogyo K.K. and PT90, manufactured by Tokai Carbon K.K. These particles were separately mixed with a polytetrafluoroethylene fine powder, extruded, dried and the resulting samples were drawn to produce porous ribbons. FIG. 3 indicates one of these ribbons 6 wound about a core 10. The ribbons 6 were drawn in the direction of length. Because it was conceivable that the electrical resistance might differ according to the direction of drawing, two different types of samples were cut out of the respective ribbons 6, i.e., longitudinal samples, indicated by A in FIG. 3, cut along the direction of length (draw) of the ribbon 6; and lateral samples, indicated by B in FIG. 3, cut along the direction of width of the ribbon 6.

EXAMPLE I

A first sample was an undrawn longitudinal (A) type sample in which 12 weight percent MA600 was mixed with the polytetrafluoroethylene.

EXAMPLE II

This sample was an undrawn longitudinal (A) type sample in which 12 weight percent PT90 (described above) was mixed with polytetrafluoroethylene.

EXAMPLE III

This sample was an undrawn lateral (B) type sample in which 12 weight percent PT90 was mixed with polytetrafluoroethylene.

EXAMPLE IV

This sample was a longitudinal (A) type sample made porous by drawing to a draw ratio of 1.4 times, in which 30 weight percent PT90 was mixed with the polytetrafluoroethylene.

EXAMPLE V

This sample was a lateral (B) type sample made porous by drawing to a draw ratio of 1.4 times, in which 30 weight percent PT90 was mixed with polytetrafluoroethylene.

EXAMPLE VI

This sample was a longitudinal (A) type sample made porous by drawing to a draw ratio of 1.4 times, in which 40 weight percent MA600 was mixed with polytetrafluoroethylene.

EXAMPLE VII

This sample was a lateral (B) type sample made porous by drawing to a draw ratio of 1.4 times, in which 40 weight percent MA600 was mixed with polytetrafluoroethylene.

Figure 4:
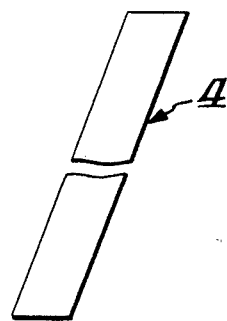
FIG. 4 is an oblique view of the tape material used in the examples.
Figure 5:
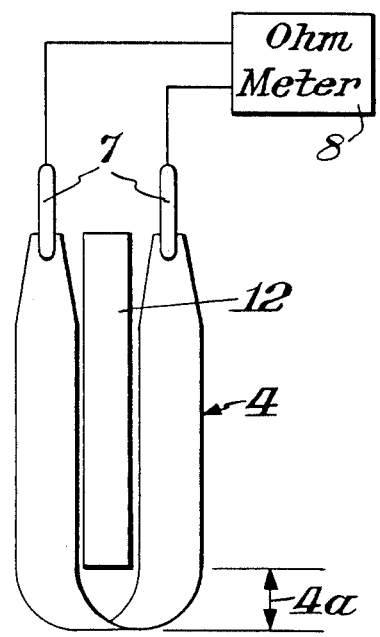
FIG. 5 is a schematic diagram of the experiments referred to in the examples.

FIG. 4 illustrates the sample tapes 4. The ends of each sample material 4 were folded in the direction of width, and were separately clamped by clips 7 as shown in FIG. 5. These clips 7 were connected to a digital multipurpose-meter 8 which measured electrical resistance. Each sample material 4 was suspended in a U-form, and an areas 4a with a height of 10 mm from the bottom of the "U" was immersed in grade C heavy oil. The grade C heavy oil was heated to a temperature of approximately 50° C., and the change in electrical resistance was recorded every 10 seconds for each sample.

A polytetrafluoroethylene sheet 12 was interposed between the left and right portions of each U-form sample material 4 above the surface of the oil so that the legs of the "U" portions would not contact each other and short circuit.

Figure 6:
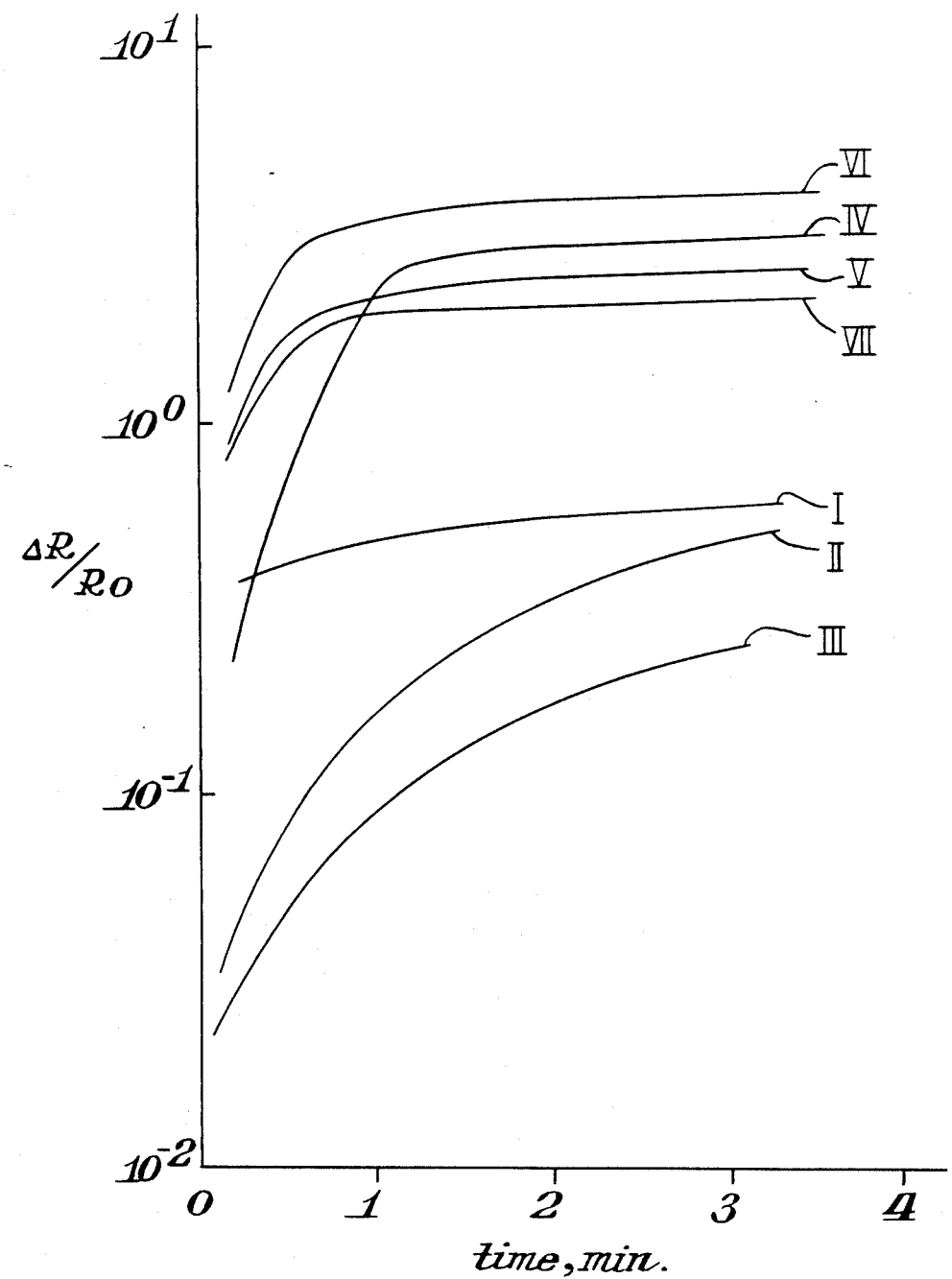
FIG. 6 is a graph showing the results of the experiments.

FIG. 6 shows the rate of change in electrical resistance $\Delta R/Ro$ measured for each of the aforementioned samples I through VII from the time of initial immersion in the aforementioned grade C heavy oil. The symbols I through VII in FIG. 6 indicate the rates of change in electrical resistance for the corresponding samples I through VII mentioned above.

It is seen from FIG. 6 that the rate of change in electrical resistance is increased, and that sensitivity is improved, in cases where the polytetrafluoroethylene is made porous by drawing, compared to cases where the polytetrafluoroethylene is not made porous by drawing. It can also be seen that in the case of the same material, samples cut along the direction of drawing, type A in FIG. 3, show additional improved superior sensitivity.

As described above, the present invention improves the permeability of an oil leakage sensor element by high-viscosity oils, and also increases the contact of such oils with the aforementioned carbon particles. As a result, the rate of change in the electrical resistance value of the oil leakage sensor element of the present invention is substantially increased, and the sensitivity of the element is improved approximately eightfold as shown by the above experiments.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. An oil leakage sensor element comprising a plurality of electrical conductors contained within and separated from each other by a continuously porous, stretched polytetrafluoroethylene (PTFE) material containing from 15 to 40 weight percent carbon particles, said carbon particles having irregular shapes and average diameter between 10 and 30 millimicrons, at least a portion of the exterior surfaces of the carbon particles being exposed at the pore walls of the PTFE and extending into said pores.

2. The sensor element of claim 1 in which said porous, stretched PTFE material is an extruded PTFE film containing said carbon particles which is stretched, after removal of lubricant, to an extent of 1.5 times or less its unstretched length.

3. The sensor element of claim 1 connected between electrodes, which electrodes are connected to resistance metering apparatus.

4. The sensor element of claim 3 wherein said electrodes are wires and said element is connected to said wires such that the direction of stretch of said material is aligned with the lengthwise direction of said wires.

5. The sensor element of claim 2 in which said material is stretched to an extent of 1.2 to 1.4 times its unstretched length.

6. The sensor element of claim 5 in which said material is stretched to an extent of 1.3 times its unstretched length.

* * * * *